(12) United States Patent
Thieme et al.

(10) Patent No.: US 9,209,628 B2
(45) Date of Patent: Dec. 8, 2015

(54) SYSTEMS AND METHODS FOR DE-ENERGIZING BATTERY PACKS

(71) Applicant: Johnson Controls Technology LLC, Wilmington, DE (US)

(72) Inventors: Bryan L. Thieme, Colgate, WI (US); Edward J. Soleski, Mequon, WI (US); William M. Cavanaugh, Sussex, WI (US); Dharmendra B. Patel, Sussex, WI (US); Thomas M. Watson, Milwaukee, WI (US)

(73) Assignee: Johnson Controls Technology LLC, Wilmington, DE (US)

( * ) Notice: Subject to any disclaimer, the term of this patent is extended or adjusted under 35 U.S.C. 154(b) by 356 days.

(21) Appl. No.: 13/736,571

(22) Filed: Jan. 8, 2013

(65) Prior Publication Data

US 2013/0175999 A1  Jul. 11, 2013

Related U.S. Application Data

(60) Provisional application No. 61/584,576, filed on Jan. 9, 2012.

(51) Int. Cl.
*H02J 7/00* (2006.01)
*H02J 9/00* (2006.01)
(Continued)

(52) U.S. Cl.
CPC .............. *H02J 7/00* (2013.01); *B60L 3/0046* (2013.01); *B60L 3/04* (2013.01); *B60S 5/06* (2013.01);
(Continued)

(58) Field of Classification Search
CPC ............ H02J 7/00; H02J 9/00; G01N 27/416; H04Q 1/30; B60L 3/04; B60L 3/0046; Y02T 90/124; Y02T 10/7065; B60S 5/06

USPC .......... 320/136, 104, 118, 125, 124; 324/426; 340/636.1; 307/66, 150
See application file for complete search history.

(56) References Cited

U.S. PATENT DOCUMENTS 4,407,909 A    10/1983  Goebel
4,504,082 A *  3/1985  Brown et al. ................. 280/735
(Continued)

FOREIGN PATENT DOCUMENTS

DE   102009058884 A1   7/2010
DE   102010020911 A1   11/2011
(Continued)

OTHER PUBLICATIONS

Cierullies (English Machine Translation of German Patent Document No. DE102009058884, published Jul. 29, 2010, translated on Feb. 22, 2015 by EPO Patent Machine Translator, 11 pages).*

(Continued)

*Primary Examiner* — Phallaka Kik
(74) *Attorney, Agent, or Firm* — Fletcher Yoder, P.C.

(57) ABSTRACT

Systems and methods for de-energizing battery packs in vehicles that receive at least a portion of their motive power from electricity generated from a battery are provided. By way of example, one embodiment includes a battery de-energizer that is configured to electrically couple to a port or receptacle, such as the service disconnect receptacle, on the vehicle and discharge the electrical energy stored in the battery pack. Another embodiment includes a battery management unit (BMU) designed to monitor one or more sensors to determine if a crash has occurred. If a crash is determined, the BMU electrically couples a battery de-energizer circuit to the battery pack to discharge the electrical energy stored in the battery pack.

19 Claims, 6 Drawing Sheets

(51) Int. Cl.
 *G01N 27/416* (2006.01)
 *H04Q 1/30* (2006.01)
 *B60L 3/04* (2006.01)
 *B60S 5/06* (2006.01)
 *B60L 3/00* (2006.01)

(52) U.S. Cl.
 CPC ............ *H02J 7/0026* (2013.01); *G01N 27/416* (2013.01); *H04Q 1/30* (2013.01); *Y02T 10/7055* (2013.01); *Y02T 90/124* (2013.01)

(56) References Cited

U.S. PATENT DOCUMENTS

| | | | | |
|---|---|---|---|---|
| 5,164,653 | A * | 11/1992 | Reem | 320/135 |
| 5,366,241 | A * | 11/1994 | Kithil | 280/735 |
| 5,995,891 | A * | 11/1999 | Mayumi et al. | 701/45 |
| 6,107,779 | A * | 8/2000 | Hara et al. | 320/132 |
| 6,270,916 | B1 | 8/2001 | Sink et al. | |
| 6,900,615 | B2 | 5/2005 | Kamenoff | |
| 7,164,257 | B2 * | 1/2007 | Johnson et al. | 320/134 |
| 7,190,147 | B2 | 3/2007 | Gileff et al. | |
| 8,212,524 | B2 * | 7/2012 | Ha et al. | 320/118 |
| 2003/0029654 | A1 * | 2/2003 | Shimane et al. | 180/65.4 |
| 2003/0107861 | A1 * | 6/2003 | Hazelton | 361/92 |
| 2003/0151387 | A1 * | 8/2003 | Kumar | 320/104 |
| 2005/0083018 | A1 * | 4/2005 | Morrow | 320/128 |
| 2007/0041140 | A1 * | 2/2007 | Furukawa | 361/115 |
| 2007/0252435 | A1 * | 11/2007 | Coe et al. | 307/10.1 |
| 2008/0084187 | A1 * | 4/2008 | Cutrona | 320/132 |
| 2008/0290842 | A1 * | 11/2008 | Davis et al. | 320/166 |
| 2009/0146610 | A1 * | 6/2009 | Trigiani | 320/119 |
| 2010/0106351 | A1 * | 4/2010 | Hanssen et al. | 701/22 |
| 2010/0134069 | A1 * | 6/2010 | Oosawa et al. | 320/118 |
| 2011/0204720 | A1 * | 8/2011 | Ruiz et al. | 307/66 |
| 2012/0025620 | A1 * | 2/2012 | Stump et al. | 307/80 |
| 2012/0053774 | A1 * | 3/2012 | Maini et al. | 701/22 |
| 2012/0068532 | A1 * | 3/2012 | Tanabe et al. | 307/10.1 |
| 2012/0313560 | A1 | 12/2012 | Hambitzer et al. | |
| 2012/0323417 | A1 * | 12/2012 | Rumer et al. | 701/22 |
| 2013/0017421 | A1 * | 1/2013 | Onnerud et al. | 429/61 |
| 2013/0054061 | A1 * | 2/2013 | Nishimoto | 701/22 |
| 2013/0127421 | A1 | 5/2013 | Doring et al. | |
| 2015/0008747 | A1 * | 1/2015 | Salcone | 307/66 |

FOREIGN PATENT DOCUMENTS

| | | | | |
|---|---|---|---|---|
| EP | 2337182 | A2 | 6/2011 | |
| EP | 2355229 | A1 | 8/2011 | |
| JP | 2008176967 | A | 7/2008 | |
| JP | 2010182619 | A | 8/2010 | |
| JP | 2010183679 | A * | 8/2010 | ............... H02J 7/00 |
| WO | 2008/032945 | A1 | 3/2008 | |

OTHER PUBLICATIONS

Hiroyashu (English Machine Translation of Japanese Patent Document No. JP 2010-182619 A, published Aug. 19, 2010, tranlsated on Feb. 22, 2015 by JPO Patent Machine Translator, 11 pages).*

International Search Report and Written Opinion for PCT Application No. PCT/US2013/020738 dated Jul. 5, 2013, 14 pgs.

Jack Thornton; "Charging Forward," Mechanical Engineering, Aug. 2012, pp. 36-39.

* cited by examiner

SYSTEMS AND METHODS FOR DE-ENERGIZING BATTERY PACKS

CROSS REFERENCE TO RELATED APPLICATIONS

This application claims priority to and the benefit of U.S. Provisional Application Ser. No. 61/584,576, entitled "BATTERY PACK DE-ENERGIZER PLUG AND RECEPTACLE", filed Jan. 9, 2012, which is hereby incorporated by reference in its entirety for all purposes.

BACKGROUND

The present disclosure relates generally to the battery systems for vehicles deriving at least a portion of their motive power from an electrical power source. More specifically, the present disclosure relates to systems and methods for discharging the battery systems of such vehicles.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Vehicles, such as cars, trucks, and vans, are widely used to facilitate the movement of people and goods in modern society. Vehicles may utilize a number of different energy sources (e.g., a hydrocarbon fuel, a battery system, a capacitance system, a compressed air system) to produce motive power. In particular, the term "xEV" may be used to describe any vehicle that derives at least a portion of its motive power from an electric power source (e.g., a battery system). For example, electric vehicles (EVs), which may also be referred to as all-electric vehicles, typically include a battery system and use electric power for all of their motive power. As such, EVs may be principally dependent on a plug-in power source to charge a battery system, while other power generation/conservation systems (e.g., regenerative braking systems) may help extend the life of the battery and the range of the EV during operation.

Two specific sub-classes of xEV are the hybrid electric vehicle (HEV) and the plug-in hybrid electric vehicle (PHEV). Both the HEV and the PHEVs generally include an internal combustion engine in addition to a battery system. For the PHEV, as the name suggests, the battery system is capable of being charged from a plug-in power source. A series hybrid vehicle (e.g., a series PHEV or HEV) uses the internal combustion engine to turn a generator that, in turn, supplies current to an electric motor to move the vehicle. In contrast, a parallel hybrid (e.g., a parallel PHEV or HEV) can simultaneously provide motive power from an internal combustion engine and a battery powered electric drive system. That is, certain xEVs may use electrical energy stored in the battery system to boost (i.e., provide additional power to) the powertrain of the vehicle. Furthermore, xEVs (e.g., PHEVs and HEVs) may take advantage of opportunistic energy capture (e.g., via regenerative braking systems or similar energy conservation systems) in addition to using at least a portion of the power from the engine to charge the battery system.

In general, xEVs may provide a number of advantages as compared to traditional, gas-powered vehicles that solely rely on internal combustion engines for motive power. For example, xEVs may produce fewer undesirable emission products and may exhibit greater fuel efficiency as compared to vehicles using only internal combustion engines to propel the vehicle. Furthermore, for some xEVs, such as all-electric EVs that lack an internal combustion engine, the use of gasoline may be eliminated entirely.

In the event of a crash rendering an xEV inoperable, electrical energy stored in the battery packs of an xEV may no longer be useful in powering the vehicle, rendering it unnecessary to remain in the battery packs. However, accessing the battery terminals of the battery packs to discharge the electrical energy typically requires technical expertise that only a skilled technician would possess. Due to the limited number of skilled technicians, it would be desirable have an easier way to discharge the battery packs.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Present embodiments include systems and methods for discharging the battery packs in an xEV by attaching a battery pack de-energizer to an existing service disconnect of the xEV. In one embodiment, a battery de-energizer is configured to electrically couple to service disconnect receptacles of an xEV automatically and discharge electrical energy stored in the battery pack of the xEV. In another embodiment, a battery pack of an xEV includes a battery, a service disconnect receptacle, and a battery de-energizer. The battery de-energizer electrically couples to the service disconnect receptacle to discharge electrical energy stored in the battery of the battery pack. In another embodiment, a battery system of the vehicle includes a battery pack and a battery management unit (BMU) of an xEV. The BMU utilizes one or more sensors to determine if a crash or other catastrophic event has occurred. If so, the BMU sends signals to electrically couple a battery de-energizer circuit to the battery pack to discharge stored electrical energy.

DRAWINGS

Various aspects of this disclosure may be better understood upon reading the following detailed description and upon reference to the drawings in which.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

For the purposes of the present disclosure, it should be noted that the presently disclosed embodiments are particularly directed toward applications for xEV electric vehicles. As will be appreciated by those skilled in the art, hybrid electric vehicles (HEVs) combine an internal combustion engine propulsion and high voltage battery power to create fraction. A plug-in electric vehicle (PEV) is any vehicle that can be charged from an external source of electricity, such as wall sockets, and the energy stored in the rechargeable battery packs drives or contributes to drive the wheels. PEVs are a subcategory of electric vehicles that include all-electric or battery electric vehicles (BEVs), plug-in hybrid vehicles (PHEVs), and electric vehicle conversions of hybrid electric vehicles and conventional internal combustion engine vehicles. An electric vehicle (EV) is an all-electric vehicle that uses for its propulsion one or more motors powered by electric energy. The term "xEV" is defined herein to include all of the foregoing or any variations or combinations thereof that include electric power as a motive force.

As set forth above, battery packs for xEVs may include an electronic controller, such as a battery management unit (BMU), to monitor various parameters associated with the operation of the battery pack. For example, a BMU may monitor the temperature, pressure, current, voltage, capacity, and so forth, for the various battery modules and electrochemical cells (e.g., NiMH and/or lithium-ion cells) of the battery pack using a number of sensors distributed throughout the battery pack. Additionally, the BMU may communicate the monitored parameters of the battery pack to a vehicle control unit (VCU), which may generally monitor the operation of the xEV and inform the driver and/or make adjustments to the operation of the xEV in response to the monitoring.

Accordingly, present embodiments are directed towards systems and methods for discharging the electrical energy stored in the battery packs of an xEV. Systems and methods include a service disconnect disposed between two battery modules in the battery pack of the xEV. The service disconnect is removed and a battery de-energizer is plugged in its place. The battery de-energizer is left plugged into the xEV over a period of time to discharge the battery pack. Other embodiments include a battery management unit (BMU) on each battery pack and a vehicle control unit (VCU) in the xEV. Both the BMU and the VCU monitor various sensors disposed in the xEV for indication of a crash. In the event of a crash or other catastrophic event, the BMU may request that a battery de-energizer circuit be connected to discharge the battery packs of the xEV.

Figure 1:
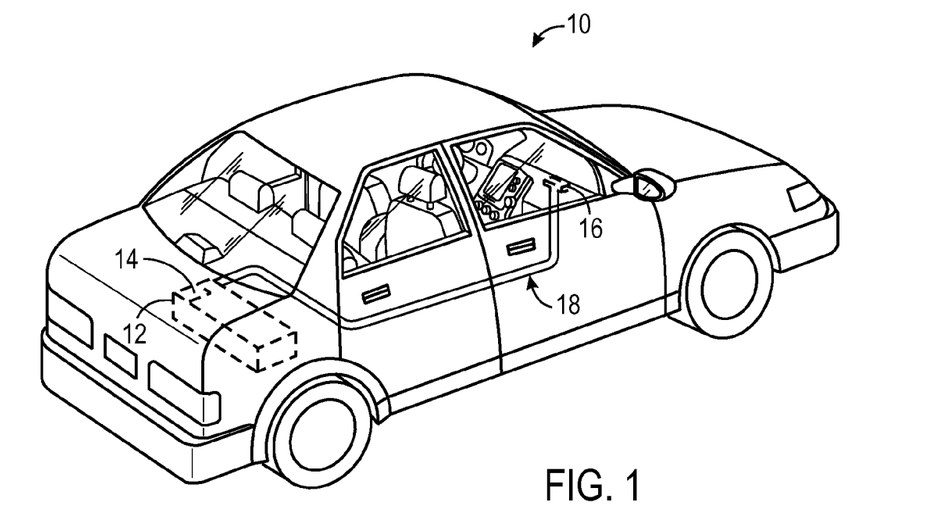
FIG. 1 is a perspective view of an xEV including a vehicle control unit (VCU), and a battery pack having a battery management unit (BMU), in accordance with an embodiment of the present disclosure.

With the foregoing in mind, FIG. 1 is a perspective view of an xEV 10 in accordance with an embodiment of a present disclosure. The illustrated xEV 10 may be any type of vehicle having a battery system for providing at least a portion of the motive power to propel the vehicle. For example, the xEV 10 may be an all-electric vehicle (EV), a hybrid electric vehicle (HEV), a plug-in hybrid electric vehicle (PHEV), or other type of vehicle using electric power to provide at least a portion of the propulsion for the vehicle. Although xEV 10 is illustrated as a car in FIG. 1, in other embodiments, other types of vehicles may be used with the present technique. For example, in other embodiments, the xEV 10 may be a truck, bus, industrial vehicle, motorcycle, recreational vehicle, boat, or any other type of vehicle that may move, at least partially, using electric power. Accordingly, xEV 10 includes a battery pack 12 capable of supplying electrical power to the xEV 10 that may be used to move the xEV 10, in addition to powering other features of the xEV 10 (e.g., lights, automatic windows, automatic locks, entertainment systems, and similar components and accessories of the xEV 10). It should be appreciated that the term "battery pack" as used herein may generally refer to a battery system that includes a number of electrochemical cells and a battery management unit (BMU) 14. It should also be appreciated that, in other embodiments, the BMU 14 may be a separate component (e.g., part of the xEV 10) that is coupled to the battery pack 12 upon installation. Furthermore, although the battery pack 12 illustrated in FIG. 1 is positioned in the trunk or rear of the xEV 10, in other embodiments, the battery pack 12 may be positioned elsewhere in the xEV 10. For example, battery pack 12 may be positioned based on the available space within the xEV 10, the desired weight balance of the xEV 10, the location of other components used with the battery pack 12 (e.g., battery management systems, vents or cooling devices, or similar systems), and similar engineering considerations.

In addition to the battery pack 12, including the BMU 14, the illustrated xEV 10 also has a vehicle control unit (VCU) 16. As mentioned above, the VCU 16 may generally monitor and control certain parameters of the xEV 10. For example, the VCU 16 may use a number of sensors to monitor the temperature inside the xEV 10, the temperature outside the xEV 10, the speed of the xEV 10, the load on the electric motor, and so forth. In certain embodiments, the VCU 16 may include sensors disposed about the xEV 10 to detect when a component of the xEV 10 is operating outside of a desired range (e.g., engine failure, transmission failure, battery failure, and so forth) and may, furthermore, notify the driver and/or disable components of the xEV 10 in response. For hybrid xEVs that include an internal combustion engine, such as HEVs and PHEVs, the VCU 16 may also monitor and control parameters of the internal combustion engine (e.g., oxygen content at the air intake, atmospheric pressure, remaining fuel, revolutions per minute, coolant temperature, and other factors affecting the performance and operation of the internal combustion engine) as well.

As mentioned, the BMU 14 and the VCU 16 communicate with each other over a vehicle bus 18. The vehicle bus 18 may comprise a system of wires configured to enable electrical signals to transmit data between the BMU 14 and the VCU 16 in the xEV 10. The communication between the BMU 14 and the VCU 16 may also be enabled through a wireless communication link. The BMU 14 and the VCU 16 may communicate over the vehicle bus 18 using a communications protocol such as the controller area network (CAN) protocol. CAN is a message-based protocol specifically designed for automotive applications.

Figure 2:
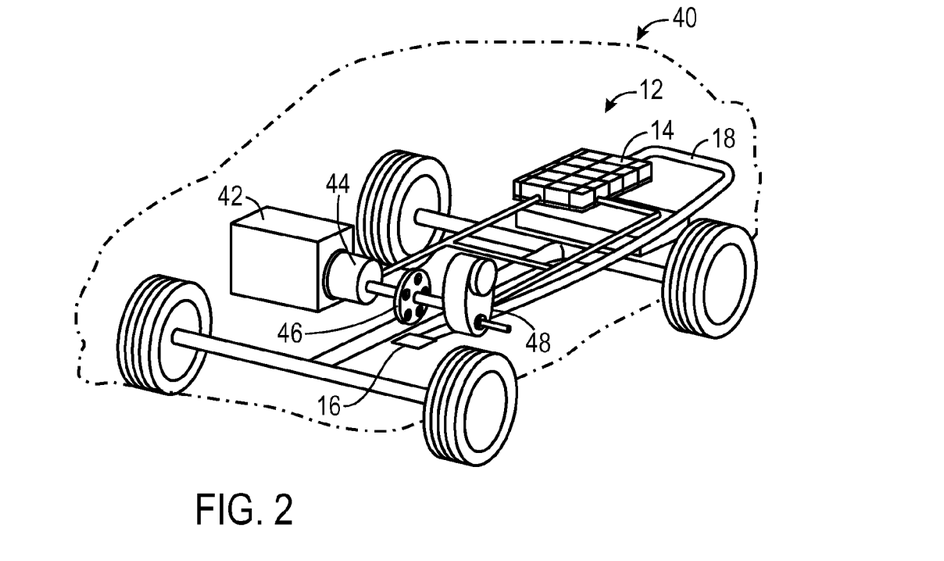
FIG. 2 is a cutaway schematic view of a hybrid electric vehicle (HEV) including battery packs with BMUs, in accordance with an embodiment of the present disclosure.

As mentioned above, xEVs, like the one illustrated in FIG. 1, may be divided into more specific sub-classes based on the internal design of the vehicle. FIG. 2 is a cutaway schematic view of a specific xEV, a hybrid electric vehicle (HEV) 40, including battery packs with BMUs, in accordance with an example embodiment of the present disclosure. Like the xEV 10 illustrated in FIG. 1, the HEV 40 includes a battery pack 12 toward the rear of the HEV 40. In certain embodiments, a plurality of battery packs 12 connected in parallel may each include a separate BMU 14. Additionally, the HEV 40 includes an internal combustion engine 42, which may combust a hydrocarbon fuel to produce power that may be used to propel the HEV 40. Also, the HEV 40 is equipped with an electric motor 44 that is coupled to the battery pack 12 and is also used to propel the HEV 40. The illustrated HEV 40 is also equipped with a power split device 46, which allows a portion of the power (e.g., rotational energy) to be directed to a generator 48 suitable for charging the battery pack 12. It should be noted that other types of xEVs (e.g., EVs, HEVs, PHEVs, etc.) and other configurations (e.g., the type of vehicle, the type of vehicle technology, and the battery chemistry, among other configurations) may be used in various embodiments of the present approach.

Figure 3:
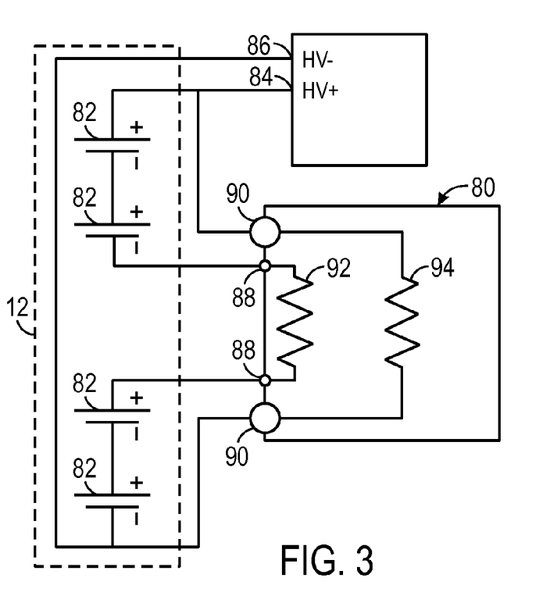
FIG. 3 is a circuit diagram of the battery de-energizer connected to the service disconnect receptacle of an xEV, in accordance with an embodiment of the present disclosure.

As mentioned above, in the event that the xEV 10, such as the HEV 40 is involved in a crash, it would be desirable to discharge the battery pack 12 easily since it is no longer needed to provide power. To discharge the battery pack 12, a battery de-energizer 80 may be connected to a service disconnect receptacle of an xEV 10, as illustrated in FIG. 3. In the embodiment of FIG. 3, the battery de-energizer 80 may be a plug. As mentioned before, the xEV 10 may include a battery pack 12 utilized to provide a portion of the motive power of the xEV. The battery pack 12 may include a plurality of battery modules 82 electrically connected in series to generate a voltage across a positive high voltage terminal 84 and a negative high voltage terminal 86. The positive high voltage terminal 84 and the negative high voltage terminal 86 may electrically couple and provide power to the power systems of the xEV 10. During normal operation of the battery pack 12, a service disconnect plug may electrically couple a first pair of service disconnect receptacles 88 to allow current to flow through the battery pack 12. During service, a technician may disengage the service disconnect plug to electrically isolate each half of the battery pack 12, allowing the technician to work on the xEV 10.

In the event of an xEV crash or other catastrophic event, any person with a battery de-energizer 80 may remove the service disconnect plug and connect the battery de-energizer 80 to the first pair of service disconnect receptacles 88 and a second pair of service disconnect receptacles 90. In certain embodiments, the second pair of service disconnect receptacles 90 may be designed to include finger-proof contacts to prevent a user from contacting the positive high voltage terminal 84 and the negative high voltage terminal 86 of the battery pack 12. Once the battery de-energizer 80 is plugged into the first pair of service disconnect receptacles 88 and the second pair of service disconnect receptacles 90, current may flow from the battery modules 82 through a first resistance 92 and a second resistance 94. In this way, over a period of time, the first resistance 92 and the second resistance 94 may dissipate the energy stored in the battery pack 12 as heat. The period of time for the battery pack to discharge may range from a few hours to several days depending upon the resistance values. A smaller resistance value for the first resistance 92 and the second resistance 94 may cause the discharge period to be longer, while a larger resistance value for the first resistance 92 and the second resistance 94 may cause the discharge period to be shorter.

Figure 4:
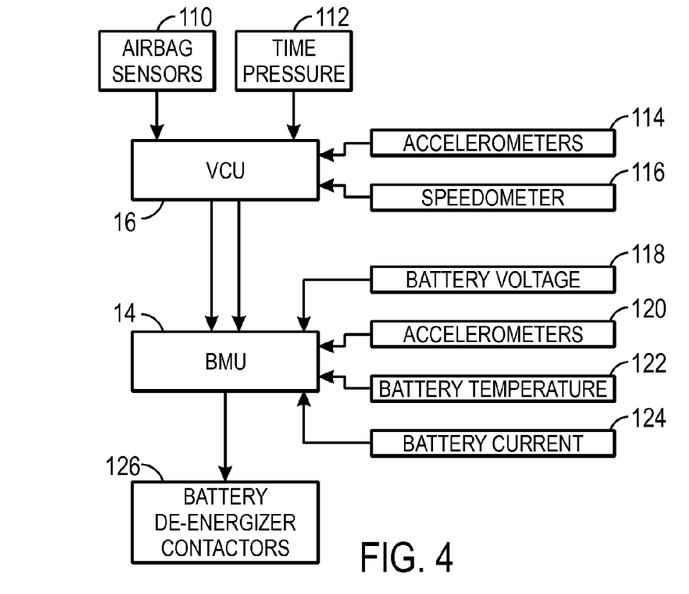
FIG. 4 is a system-level diagram illustrating the communication relationship between the VCU, the BMU, and various crash sensors, in accordance with an embodiment of the present disclosure.
Figure 5:
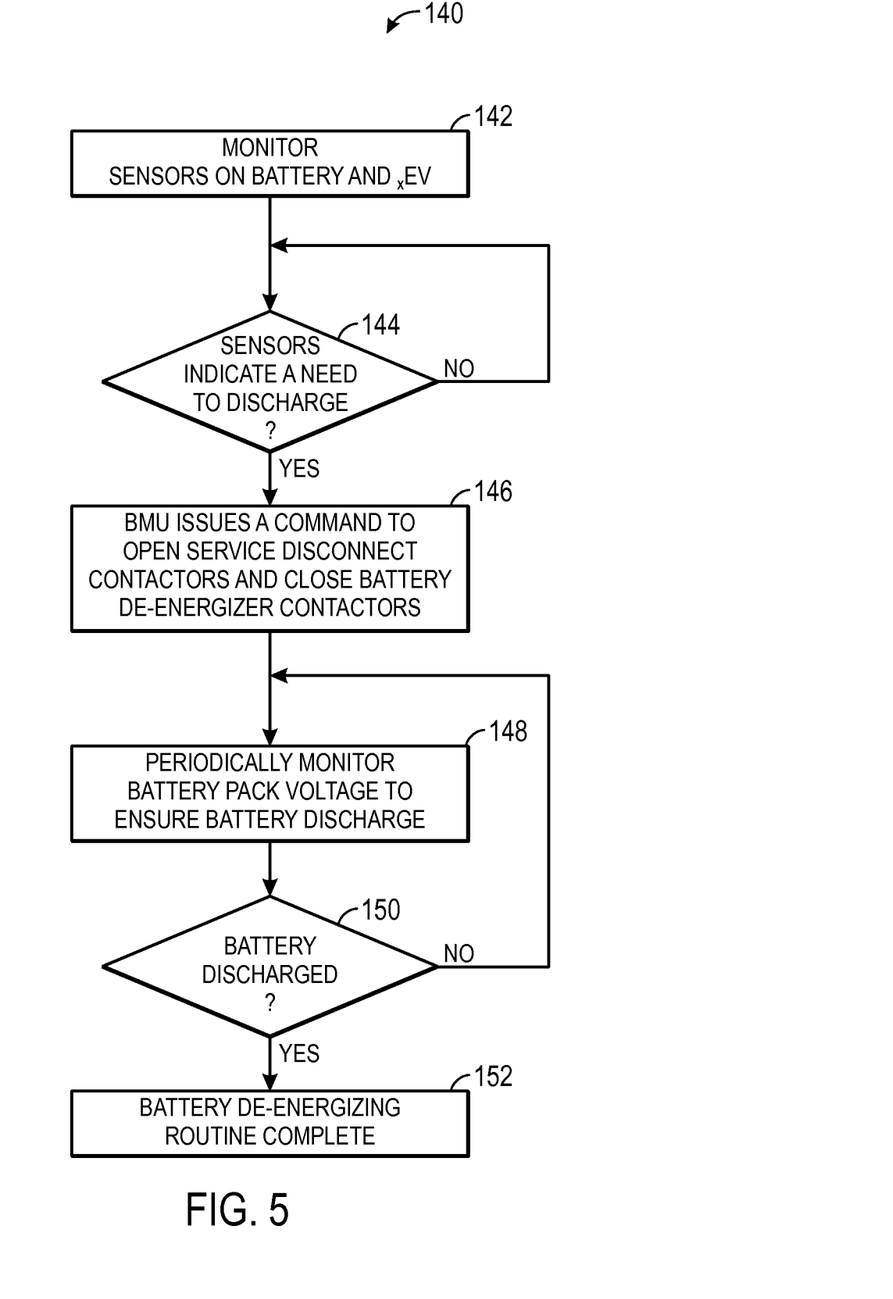
FIG. 5 is a flowchart depicting the BMU automatic discharge logic, in accordance with an embodiment of the present disclosure.

In the embodiment of FIG. 3, a person physically plugs the battery de-energizer 80 into the service disconnect receptacle to discharge the battery packs 12 of the xEV. However, in other embodiments, a battery de-energizer 80 may be automatically connected to the battery pack 12 of an xEV 10 to discharge the energy stored in the battery pack 12. FIG. 4 illustrates an embodiment of automatically discharging a battery pack 12 using a BMU 14 and a VCU 16, and FIG. 5 illustrates a flowchart 140 depicting the logic executed by the BMU 14 in automatically discharging the battery pack 12. The BMU 14 and the VCU 16 may monitor a plurality of sensors on the battery pack 12 and the xEV 10, as represented by block 142 of FIG. 5. The plurality of sensors may include airbag sensors 110, tire pressure sensors 112, accelerometers 114, and a speedometer 116 being monitored by the VCU 16, and battery voltage sensors 118, accelerometers 120, battery temperature sensors 122, and battery current sensors 124 being monitored by the BMU 14. Some of the sensors, such as the airbag sensors 110 and the speedometer 116 may be pre-existing in the xEV 10. Similarly, some of the sensors, such as the battery voltage sensors 118, battery temperature sensors 120, and the battery current sensors 122 may be usually used for other purposes rather than determining whether an xEV 10 has experienced a crash or catastrophic event. For example, a battery voltage sensor 118 on the battery pack 12 may usually be used to help determine the charge left in a particular battery module 82 of the battery pack 12.

However, if the voltage in a particular battery module 82 is greater than a pre-determined threshold, it could indicate that the battery pack 12 was damaged in a crash. Likewise, the battery current sensors 122 may be usually used to determine if the battery pack 12 can handle powering another component of the power system of the xEV 10. However, if the current inexplicably falls below or rises above pre-determined thresholds, the battery pack 12 may be damaged, indicating a crash. As represented by block 144 of FIG. 5, the BMU 14 may monitor the plurality of sensors until they indicate a need to discharge the battery pack 12.

Likewise, the VCU 16 may monitor the sensors to determine if the battery pack needs to be discharged. In some embodiments, the BMU 14 and the VCU 16 may take into account more than one sensor to determine if a crash has occurred. For example, if another vehicle collides with the xEV 10 near the battery pack, the accelerometers 120 monitored by the BMU 14 may indicate a crash, while the accelerometers 114 monitored by the VCU 16 may not indicate a crash. To give another example, if any sensor indicates a crash, but the speedometer 116 indicates that the xEV 10 is still in motion, a crash may not be determined.

In certain embodiments, the BMU 14 and the VCU 16 may communicate with each other to determine if a crash has occurred. In other embodiments, the BMU 14 or the VCU 16 may independently determine if a crash has occurred. In the case that a crash is determined by the BMU 14, the VCU 16, or a combination thereof, a crash indication signal may be sent to the BMU 14, and the BMU 14 may issue a command to open service disconnect contactors and close battery de-energizer contactors 126, as represented by block 146 of FIG. 5. As will be shown in FIG. 6, the battery de-energizer contactors 126 may automatically connect a battery de-energizer 80 to the battery pack 12 to discharge the energy stored in the battery modules 82. Once the battery pack 12 is discharging, the BMU 14 may periodically monitor the battery pack 12 voltage using the battery voltage sensors 118 to ensure it is discharging correctly, as represented by block 148 of FIG. 5. At block 150 of FIG. 5, the BMU 14 may check if the battery pack 12 is fully discharged. If not, the BMU 14 may continue to periodically monitor the battery pack 12 voltage using the battery voltage sensors 118. If the battery pack 12 is fully discharged, the battery de-energizing routine may be complete and an appropriate indication may be sent from the BMU 14 to the VCU 16 so that the state of the battery pack may be displayed, as represented by block 152 of FIG. 5.

Figure 6:
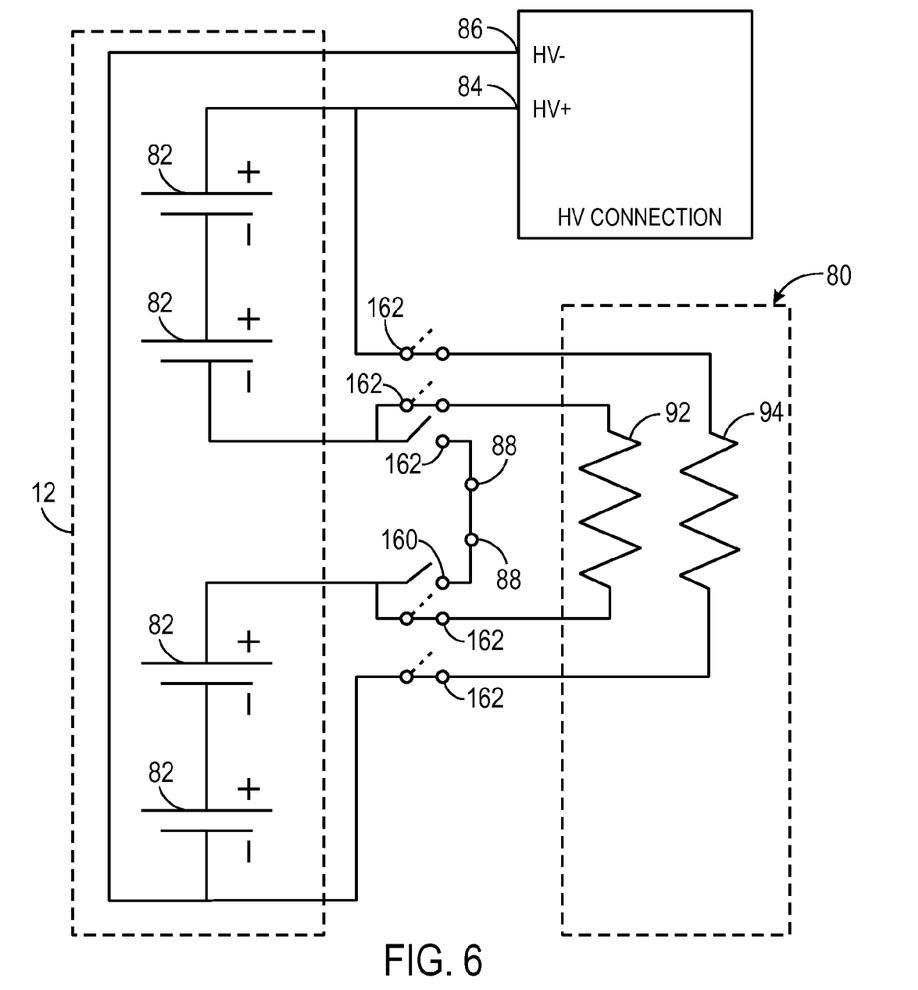
FIG. 6 is circuit diagram of a battery de-energizer that may be automatically connected to discharge a battery pack of an xEV by the BMU if a crash is detected, in accordance with an embodiment of the present disclosure.

As mentioned above, when the BMU 14, the VCU 16, or a combination thereof detects a crash, the BMU 14 may send a command to close battery de-energizer contactors 126 and connect a battery de-energizer 80 to the battery pack 12. FIG. 6 illustrates an embodiment of a circuit that may be utilized by the BMU 14 to automatically de-energize the battery pack 12 of the xEV 10. The embodiment of FIG. 6 has a similar design to the embodiment of FIG. 3, with the positive high voltage terminal 84, the negative high voltage terminal 86, the first resistance 92 and the second resistance 94. As before, a service disconnect X may be removed from the first pair of service disconnect receptacles 88 to electrically isolate two halves of the battery pack 12, reducing the voltage potential between the positive high voltage terminal 84 and the negative high voltage terminal 86.

Additionally, the embodiment of FIG. 6 includes service disconnect contactors 160 as well as battery de-energizer contactors 162. During normal operation, the service disconnect contactors 160 may form a closed circuit while the battery de-energizer contactors 162 form an open circuit. As mentioned above, in the case that the BMU 14 determines a crash or other catastrophic event, the BMU 14 may send signals to open the service disconnect contactors 160 and close the battery de-energizer contactors 162, allowing current from the battery pack 12 to flow through the first resistance 92 and the second resistance 94 and effectively de-energizing the battery pack 12. The energy stored in the battery pack 12 may be dissipated in the battery de-energizer 80 as heat. In other embodiments, the battery de-energizer may include more than two resistances or more complex impedances.

Figure 7:
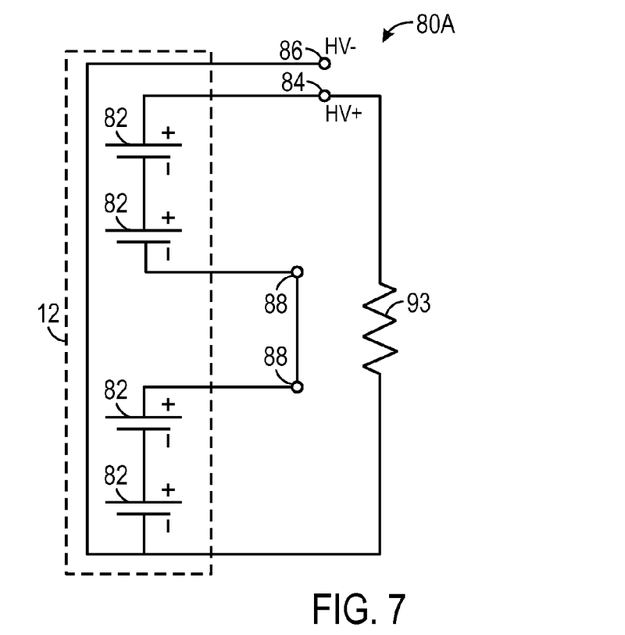
FIG. 7 is a circuit diagram of the battery de-energizer connected to the high voltage connector of an xEV, in accordance with an embodiment of the present disclosure.

Although the embodiments described above involve connecting a battery de-energizer 80 to a service disconnect receptacle of the xEV 10, other receptacles or ports of the battery pack 12 of the xEV 10 may be used to dissipate the energy stored in the battery pack 12. As one example, FIG. 7 illustrates a battery de-energizer 80A connected to the high voltage port, specifically the positive high voltage terminal 84. In this embodiment, the battery de-energizer 80A may be a plug, although in other embodiments it may be automatically connected under certain circumstances, e.g., a vehicle crash, in accordance with the teachings set forth with regard to FIGS. 4-6. If it is desired to discharge the battery pack 12, a technician may attach the battery de-energizer 80A to the positive high voltage terminal 84 so that the energy in the battery pack 12 may be dissipated through the resistance 93.

Figure 8:
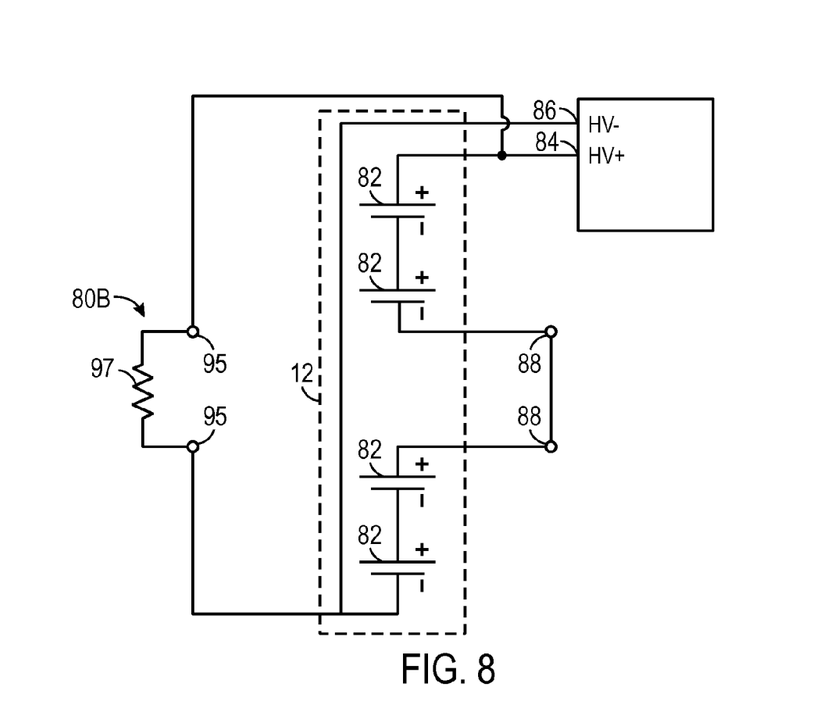
FIG. 8 is a circuit diagram of the battery de-energizer connected to the charger port of an xEV, in accordance with an embodiment of the present disclosure.

As another example, FIG. 8 illustrates a battery de-energizer 80B connected to the charger port 95 of the xEV 10. In this embodiment, the battery de-energizer 80B may be a plug, although in other embodiments it may be automatically connected under certain circumstances, e.g., a vehicle crash, in accordance with the teachings set forth with regard to FIGS. 4-6. If it is desired to discharge the battery pack 12, someone may attach the battery de-energizer 80B to the charger port 95 so that the energy in the battery pack 12 may be dissipated through the resistance 97. It should be recognized that this embodiment uses a receptacle or port of the xEV 10 that is easily accessible by anyone, unlike the earlier embodiments where the receptacle or port is typically only accessible by a technician or someone familiar with servicing the battery pack 12 and/or xEV 10. Indeed, since the battery de-energizer 80B may be coupled to the charger port 95 of the xEV 10, anyone, including the driver of the xEV 10, could easily begin to discharge the battery pack 12 by simply plugging the battery de-energizer 80B into the charger port 95.

Figure 9:
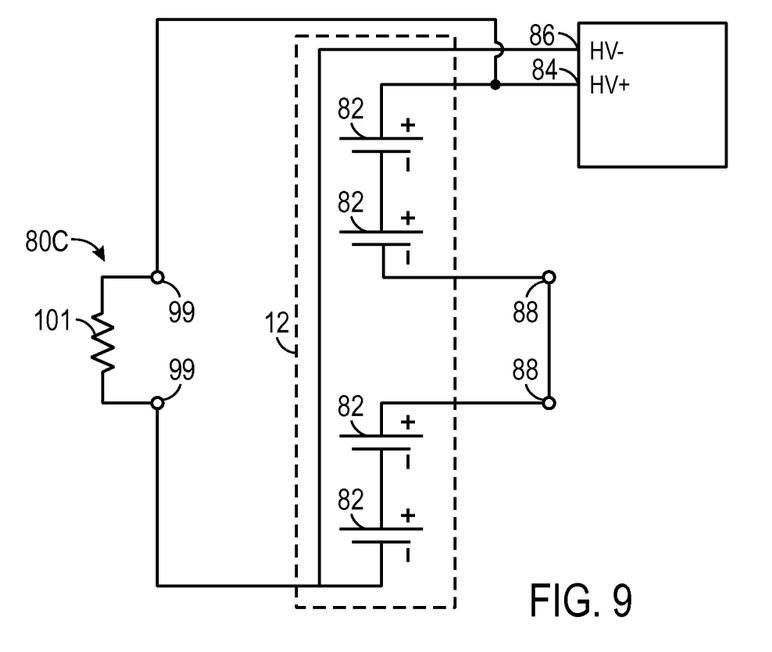
FIG. 9 is a circuit diagram of the battery de-energizer connected to a special discharge port of an xEV, in accordance with an embodiment of the present disclosure.

As yet another example, FIG. 9 illustrates a battery de-energizer 80C connected to a special discharge port 99 of the battery pack 12 of the xEV 10. In this embodiment, the battery de-energizer 80C may be a plug although in other embodiments it may be automatically connected under certain circumstances, e.g., a vehicle crash, in accordance with the teachings set forth with regard to FIGS. 4-6. If it is desired to discharge the battery pack 12, someone may attach the battery de-energizer 80C to the special discharge port 99 so that the energy in the battery pack 12 may be dissipated through the resistance 101. Unlike the previous embodiments where an existing receptacle or port of the battery pack 12 and/or xEV 10 is used to couple to a battery de-energizer 80 to dissipate the energy in the battery pack 12, the present embodiment uses an additional port to accomplish this task. Indeed, it may be desirable to use a special discharge port 99 instead of an existing receptacle or port simply to provide separate ports, each being dedicated to a single function. Furthermore, the special discharge port 99 may be one that is accessible by anyone, including a driver of the xEV 10, or it may be one that is accessible only by a technician or someone else familiar with servicing the battery pack 12 and/or xEV 10.

While only certain features and embodiments of the invention have been illustrated and described, many modifications and changes may occur to those skilled in the art (e.g., variations in sizes, dimensions, structures, shapes and proportions of the various elements, values of parameters (e.g., temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

The invention claimed is:

1. A battery de-energizer system, comprising:
a battery de-energizer circuit configured to electrically couple to service disconnect receptacles of a battery pack for a vehicle that receives at least a portion of its motive power from electricity provided by the battery pack, and wherein the battery de-energizer circuit is configured to discharge electrical energy stored in the battery pack; and
a battery management unit that monitors one or more sensors and electrically couples the battery de-energizer circuit to the battery pack to discharge the electrical energy stored in the battery pack based on signals supplied by the one or more sensors, wherein the battery management unit causes one or more battery de-energizer contactors to close to electrically couple the battery de-energizer circuit to the battery pack.

2. The system of claim 1, wherein the battery de-energizer circuit is configured to dissipate the electrical energy stored in the battery pack as heat.

3. The system of claim 1, wherein the battery de-energizer circuit comprises resistive elements configured to discharge the electrical energy stored in the battery pack.

4. A battery pack comprising:
a service disconnect receptacle configured to form an open circuit between a plurality of battery modules when a service disconnect plug is electrically decoupled from the service disconnect receptacle;
a battery de-energizer configured to electrically couple to the service disconnect receptacles and discharge electrical energy stored in the plurality of battery modules; and
a battery management unit configured to monitor one or more sensors and electrically couple the battery de-energizer to the plurality of battery modules by causing one or more battery de-energizer contactors to close based on signals from the one or more sensors.

5. The battery pack of claim 4, wherein the battery de-energizer is configured to dissipate the electrical energy stored in the plurality of battery modules as heat.

6. The battery pack of claim 4, wherein the battery de-energizer comprises at least one resistive element configured to to discharge the electrical energy stored in the plurality of battery modules.

7. The battery pack of claim 4, a wherein the battery management unit is configured to monitor the one or more sensors to determine if a crash has occurred, and electrically couple the battery de-energizer to the battery pack if the crash has occurred.

8. The battery pack of claim 4, wherein the battery de-energizer comprises a plug.

9. The battery pack of claim 4, wherein the service disconnect receptacle comprises a pair of terminals between the plurality of battery modules of the battery pack, and a pair of terminals coupled to the terminals of the battery pack, and wherein the battery de-energizer electrically couples to both pairs of terminals to discharge the electrical energy stored in the battery pack.

10. The battery pack of claim 4, wherein the one or more sensors comprise one or more accelerometers that indicate a crash to the battery management unit if the one or more accelerometers exceed a pre-determined force threshold.

11. The battery pack of claim 4, wherein the one or more sensors comprise one or more temperature sensors that indicate a crash to the battery management unit if they exceed a pre-determined temperature threshold.

12. The battery pack of claim 4, wherein the one or more sensors comprise one or more voltage sensors that indicate a crash to the battery management unit if the measured voltage exceeds a pre-determined threshold.

13. The battery pack of claim 4, wherein the one or more sensors comprise one or more current sensors that indicate a crash to the battery management unit if the measured current falls below or rises above pre-determined thresholds.

14. The battery pack of claim 4, wherein the battery management unit takes a combination of two or more inputs from the one or more sensors into consideration to determine if a crash has occurred.

15. The battery system of claim 4, comprising a vehicle control unit configured to monitor one or more additional sensors, determine if a crash has occurred, and send a crash indication signal to the battery management unit if a crash is determined.

16. The battery system of claim 15, wherein the one or more additional sensors comprise airbag sensors to determine if the crash has occurred.

17. A method for discharging a battery pack of a vehicle that receives at least a portion of its motive power from electricity generated from the battery pack comprising:
monitoring one or more sensors to determine if a crash has occurred; and
sending a signal to electrically couple a battery de-energizer circuit to the battery pack if the crash has occurred to discharge electrical energy stored in the battery pack, wherein electrically coupling the battery de-energizer circuit to the battery pack comprises causing one or more battery de-energizer contactors to close.

18. The method of claim 17 comprising monitoring a voltage of the battery pack to ensure the battery pack is discharging the electrical energy correctly.

19. The method of claim 17 comprising sending a signal to service disconnect contactors to open to decouple a service disconnect from the battery pack while the battery pack is discharging.

* * * * *